(12) United States Patent
Cheng et al.

(10) Patent No.: US 9,389,199 B2
(45) Date of Patent: Jul. 12, 2016

(54) BACKSIDE SENSING BIOFET WITH ENHANCED PERFORMANCE

(71) Applicant: Taiwan Semiconductor Manufacturing Company, Ltd., Hsin-Chu (TW)

(72) Inventors: Chun-Wen Cheng, Zhubei (TW); Yi-Shao Liu, Zhubei (TW); Fei-Lung Lai, New Taipei (TW); Wei-Cheng Lin, Zhubei (TW); Ta-Chuan Liao, Taichung (TW); Chien-Kuo Yang, Taipei (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 176 days.

(21) Appl. No.: 13/905,912

(22) Filed: May 30, 2013

(65) Prior Publication Data

US 2014/0264467 A1 Sep. 18, 2014

Related U.S. Application Data

(60) Provisional application No. 61/785,055, filed on Mar. 14, 2013.

(51) Int. Cl.
*G01N 27/414* (2006.01)

(52) U.S. Cl.
CPC ................... *G01N 27/4148* (2013.01)

(58) Field of Classification Search
USPC .............................. 257/252, 253, 262; 438/49
See application file for complete search history.

(56) References Cited

U.S. PATENT DOCUMENTS

| 8,728,844 | B1 | 5/2014 | Liu et al. |
|---|---|---|---|
| 8,900,905 | B1 | 12/2014 | Liu et al. |
| 2002/0127623 | A1 | 9/2002 | Minshull et al. |
| 2004/0238379 | A1 | 12/2004 | Lindsay et al. |
| 2005/0156207 | A1 | 7/2005 | Yazawa et al. |
| 2006/0278528 | A1 | 12/2006 | Fleischer et al. |
| 2009/0008629 | A1 | 1/2009 | Matsumoto et al. |
| 2009/0095968 | A1 | 4/2009 | Baek et al. |
| 2011/0316565 | A1 | 12/2011 | Guo et al. |
| 2012/0032235 | A1 | 2/2012 | Bikumandla |

(Continued)

FOREIGN PATENT DOCUMENTS

| CN | 102659752 A | 9/2012 |
|---|---|---|
| TW | 201224478 | 6/2012 |

OTHER PUBLICATIONS

Chung, Wen-Yaw et al., "A New Body-Effect Elimination Technique for ISFET Measurement," 2005 IEEE Sensors, Oct. 30, 2005-Nov. 3, 2005, pp. 1046-1049.

*Primary Examiner* — Hrayr A Sayadian
(74) *Attorney, Agent, or Firm* — Slater Matsil, LLP

(57) ABSTRACT

The present disclosure provides a bio-field effect transistor (BioFET) and a method of fabricating a BioFET device. The method includes forming a BioFET using one or more process steps compatible with or typical to a complementary metal-oxide-semiconductor (CMOS) process. The BioFET device includes a substrate, a transistor structure having a treated layer adjacent to the channel region, an isolation layer, and a dielectric layer in an opening of the isolation layer on the treated layer. The dielectric layer and the treated layer are disposed on opposite side of the transistor from a gate structure. The treated layer may be a lightly doped channel layer or a depleted layer.

17 Claims, 16 Drawing Sheets

(56) References Cited

U.S. PATENT DOCUMENTS

| | | |
|---|---|---|
| 2012/0045368 A1 | 2/2012 | Hinz et al. |
| 2013/0105868 A1 | 5/2013 | Kalnitsky et al. |
| 2013/0200438 A1 | 8/2013 | Liu et al. |
| 2014/0073039 A1 | 3/2014 | Chang et al. |
| 2014/0256030 A1 | 9/2014 | Shen et al. |
| 2014/0264467 A1 | 9/2014 | Cheng et al. |
| 2014/0308752 A1 | 10/2014 | Chang et al. |

BACKSIDE SENSING BIOFET WITH ENHANCED PERFORMANCE

RELATED CASES

This application claims priority to U.S. Provisional Patent Application No. 61/785,055, filed Mar. 14, 2013, and entitled "Backside Sensing BioFET with Enhanced Performance," which application is incorporated herein by reference.

FIELD

This disclosure relates to biosensors and methods for forming bio-chips. Particularly, this disclosure relates to bio-chips having biosensors and fluidic devices and methods for forming them.

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and microelectromechanical systems (MEMS).

Biochips are essentially miniaturized laboratories that can perform hundreds or thousands of simultaneous biochemical reactions. Biochips can detect particular biomolecules, measure their properties, process the signal, and may even analyze the data directly. Biochips enable researchers to quickly screen large numbers of biological analytes in small quantities for a variety of purposes, from disease diagnosis to detection of bioterrorism agents. Advanced biochips use a number of biosensors along with microfluidics to integrate reaction, sensing and sample management. BioFETs (biological field-effect transistors, or bio-organic field-effect transistors) are a type of biosensor that includes a transistor for electrically sensing biomolecules or bio-entities. While BioFETs are advantageous in many respects, challenges in their fabrication and/or operation arise, for example, due to compatibility issues between the semiconductor fabrication processes, the biological applications, restrictions and/or limits on the semiconductor fabrication processes, sensitivity and resolution of the electrical signals and biological applications, and/or other challenges arising from implementing a large scale integration (LSI) process.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
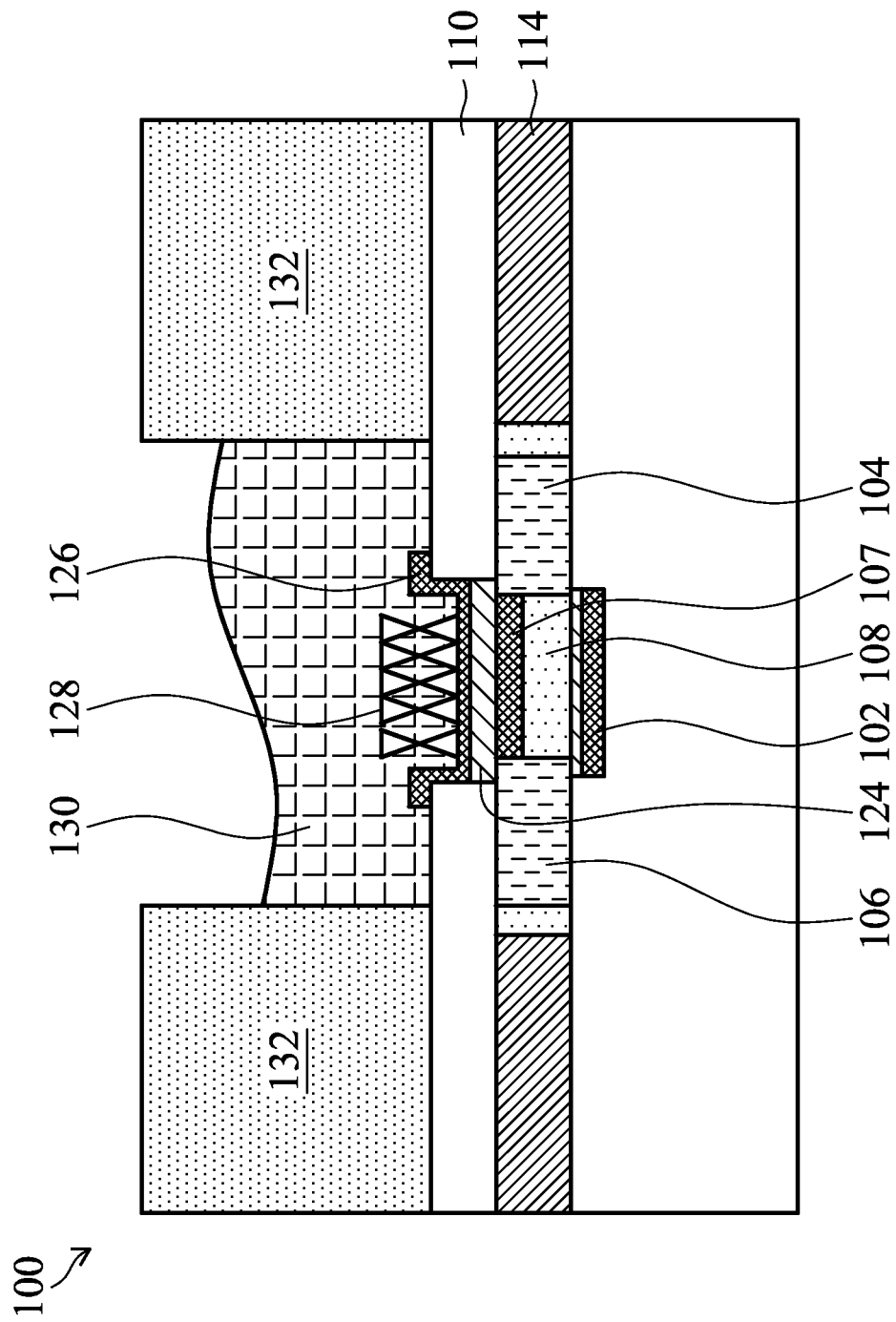
FIG. 1 is a cross-sectional view of an embodiment of a BioFET device according to one or more aspects of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Further still, references to relative terms such as "top", "front", "bottom", and "back" are used to provide a relative relationship between elements and are not intended to imply any absolute direction. Various features may be arbitrarily drawn in different scales for simplicity and clarity.

In a BioFET, the gate of a MOSFET (metal-oxide-semiconductor field-effect transistor), which controls the conductance of the semiconductor between its source and drain contacts, is replaced by a bio- or biochemical-compatible layer or a biofunctionalized layer of immobilized probe molecules that act as surface receptors. Essentially, a BioFET is a field-effect biosensor with a semiconductor transducer. An advantage of BioFETs is the prospect of label-free operation. Use of BioFETs avoids costly and time-consuming labeling operations such tagging analytes with fluorescent or radioactive probes.

Binding of a target biomolecule or bio-entity to the gate or a receptor molecule immobilized on the gate of the BioFET modulates the conductance of the BioFET. When the target biomolecule or bio-entity is bonded to the gate or the immobilized receptor, the drain current of the BioFET is varied by the gate potential, which depends on the type and amount of target bound. This change in the drain current can be measured and used to determine the type and amount of the bonding between the receptor and the target biomolecule or the biomolecule itself. A variety of receptors may be used to functionalize the gate of the BioFET such as ions, enzymes, antibodies, ligands, receptors, peptides, oligonucleotides, cells of organs, organisms and pieces of tissue. For instance, to detect ssDNA (single-stranded deoxyribonucleic acid), the gate of the BioFET may be functionalized with immobilized complementary ssDNA strands. Also, to detect various proteins such as tumor markers, the gate of the BioFET may be functionalized with monoclonal antibodies.

One example of a biosensor has a sensing surface as a top of a floating gate connected to the gate of the BioFET. The floating gate is connected to the gate structure of the BioFET through a stack of metal interconnect lines and vias (or multilayer interconnect, MLI). The various metal layers over the gate electrode can also contribute to damage by antenna effect during the MLI formation process. In such a BioFET, the potential-modulating reaction takes place at an outer surface of the final (top) metal layer or a dielectric surface formed on top of the MLI and is sensed indirectly by the BioFET. The sensitivity of the device is lower than other biosensors because of parasitic capacitances associated with the MLI. As result a sensing plate dimension is usually specified so that a sufficiently detectable amount of potential-modulating reaction can take place on the sensing plate. The minimum sensing plate dimension in turn limits the BioFET density.

In another example, the biomolecules bind directly or through receptors on the gate or the gate dielectric of the BioFET. These "direct sensing" BioFETs directly senses the target biomolecules without the parasitic capacitances associated with MLI. Its construction requires removal of the MLI material above the BioFET to form a sensing well and exposes the gate electrode or gate dielectric to the fluidic environment where potential-modulating surface reactions occur. These BioFETs are more sensitive than the floating gate types but are challenging to construct for several reasons. The sensing well etched has a high aspect ratio, for example, 30 or greater, so it is usually performed with high energy plasma etch. The high-aspect ratio of the sensing well also limits the profile of the etched sensing well. The high energy plasma etch can damage the gate electrode due to charge-induced damage. One attempt in reducing the aspect ratio of the sensing well to make the etch easier results in limitation of the number of metal layers, down to one or two metal layers. The reduction in metal layers limits the interconnect routing and integration options of the device, for example, the number and type of circuits for controlling the BioFET. The process is also very sensitive to alignment, because misalignment may expose the metals in the MLI surrounding sensing well or cause the sensing surface area to be smaller than designed.

In yet another example, the biomolecules are placed close to the gate on a backside of the substrate. In this example, a gate and sensing surface are formed on the backside of the channel region through backside of the substrate as a fluidic gate. This example avoids the difficulty of having to etch through multiple layers of interconnects and yet placing the biomolecules proximate to the gate to have much higher sensitivity than the floating gate biosensor. This type of BioFET is referred to as the backside sensing (BSS) BioFET. The various embodiments of the present disclosure involve a BSS BioFET that includes a dopant concentration gradient in the active region under the gate between the source and drain and/or a surface treatment of the active region surface proximate to the fluidic gate. Such dopant concentration gradient allows electrical property tuning of the BSS BioFET. The active region includes a treated layer proximate to the fluidic gate and a channel region. The dopant concentration gradient may be a lightly doped layer or a depleted layer formed by adding a dopant of a different conductivity type from the rest of the channel region to a treated layer of the channel region or by deactivating dopants in a thin treated layer of the channel region. Surface treatments also include annealing under oxygen or hydrogen environments.

FIG. 1 is a schematic drawing of a backside sensing (BSS) BioFET 100. The semiconductor device 100 includes a gate structure 102 formed on substrate 114. The gate structure 102 is a back gate for the BSS BioFET. The substrate 114 further includes a source region 104, a drain region 106, and an active region 108 (e.g., including a channel region) interposing the source region 104 and the drain region 106. The gate structure 102, the source region 104, the drain region 106, and the active region 108 may be formed using suitable CMOS process technology. The gate structure 102, the source region 104, the drain region 106, and the active region 108 form a FET. A portion of the active region 108 proximate to the backside is a treated layer 107, which may be a lightly doped channel layer or a depleted layer. The treated layer 107 may include dopants not found in the rest of the active region 108. For example, for a n-MOS, the treated layer 107 may be doped with arsenic or phosphorous. For a p-MOS, the treated layer 107 may be doped with boron. The treated layer 107 may include neutralizing species that tends to deactivate dopants, for example, hydrogen to deactivate boron. The treated layer 107 may be formed by annealing to repair dangling bonds or to mitigate plasma induced defects. Anneals in an oxygen atmosphere of oxygen or ozone repairs dangling bonds. Anneals in a hydrogen atmosphere of hydrogen or deuterium mitigates mobile ions and interfacial traps from plasma-induced damage.

An isolation layer 110 is disposed on the opposing side of the substrate 114, as compared to the gate structure 102. The isolation layer 110 may be a buried oxide (BOX) layer of a silicon-on-insulator (SOI) substrate. An opening in the isolation layer 110 is substantially aligned with the active region 108. A dielectric layer 124 is disposed on the bottom of the opening on the back surface of the active region 108. The dielectric layer 124 functions as the gate dielectric for the fluidic gate and covers the surface of the treated layer 107 as well as any portion of the source and drain (106/104) not covered by the isolation layer 110.

In some embodiments, a metal crown structure 126 is disposed over the dielectric layer 124 and at least partially covering the sidewalls of the isolation layer 110. When used, the metal crown structure 126 is the sensing surface used to detect biomolecules or bio-entities. Area of the metal crown structure 126 is larger than the dielectric layer 124 and thus can accommodate more potential modulating reactions. In some embodiments, the metal crown structure 126 extends over the top corners of the opening in the isolation layer 110 and partially covers the isolation layer 110. In certain embodiments, a number of receptors are bound or amplified on the metal crown structure 126 to provide sites for detecting biomolecules or bio-entities. In other embodiments, the metal crown structure 126 surface is used to bind biomolecules or bio-entities 128 having particular affinities to the metal material. The metal-containing material for metal crown structure 126 includes tantalum, tantalum nitride, niobium, tungsten nitride, ruthenium oxide, or combinations of these. Other metals including gold and platinum may also be used. According to some embodiments, the material for the metal crown structure 126 is an ohmic metal. The semiconductor device 100 includes electrical contacts (not shown) to the source region 106, the drain region, the gate structure 102, and the gate via the metal crown structure 126. If the metal crown structure 126 is not used, then the dielectric layer 124 is an interface layer that provides binding sites for receptors.

Thus, while a conventional FET uses a gate contact to control conductance of the semiconductor between the source and drain (e.g., the channel), the semiconductor device 100 allows receptors formed on the backside of the FET device to control the conductance, while the gate structure 102 (e.g., polysilicon) acts as a back gate (e.g., source substrate or body node in a conventional FET). The back gate can control the channel electron distribution without a bulk substrate effect. Thus, if molecules attach to receptors on the fluidic gate, the resistance of the field-effect transistor channel region is altered. Either gate may be biased. A front fluidic gate electrode is located proximate to the sensing surface on the metal crown structure or on the interface layer. Therefore, the semiconductor device 100 may be used to detect one or more specific biomolecules or bio-entities in the analyte environment 130 contained in the fluidic structure 132.

By adding dopants to the treated layer 107 under the dielectric layer 124, the performance of the BioFET 100 may be tuned. According to various embodiments, when the treated layer 107 is a lightly doped layer or a depleted layer, the BioFET 100 can be made more sensitive to molecules bound to receptors or to the gate. In other words, the drain current for a gate voltage may be increased relative to a BioFET without treated layer 107. In some embodiments, the treated layer 107 provides a larger bandgap which can avoid or reduce current leakage.

The semiconductor device 100 may include additional passive components such as resistors, capacitors, inductors, and/or fuses; and other active components, including P-channel field effect transistors (pFETs), N-channel field effect transistors (nFETs), metal-oxide-semiconductor field effect transistors (MOSFETs), complementary metal-oxide-semiconductor (CMOS) transistors, high voltage transistors, and/or high frequency transistors. It is further understood that additional features can be added in the semiconductor device 100, and some of the features described below can be replaced or eliminated, for additional embodiments of the semiconductor device 100.

Figure 2A:
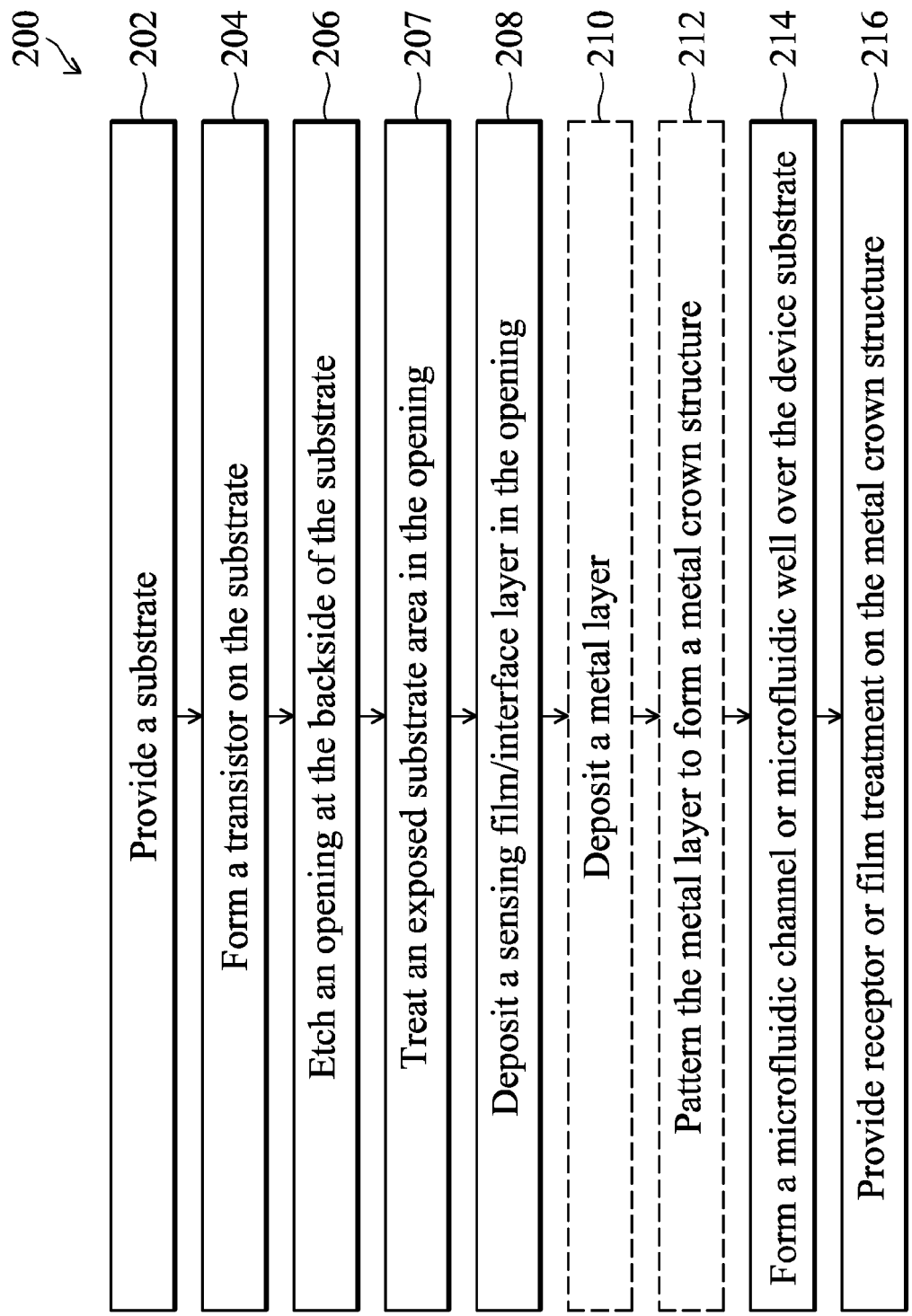
FIGS. 2A and 2B are flow charts of various embodiments of a method of fabricating a BioFET device according to one or more aspects of the present disclosure.

FIG. 2A is process flow diagram of a method 200 for making a BSS biological field effect transistor (BioFET). The method 200 includes forming a BioFET using one or more process operations compatible with or typical of complementary metal-oxide-semiconductor (CMOS) process. It is understood that additional steps can be provided before, during, and after the method 200, and some of the steps described below can be replaced or eliminated in different embodiments of the present disclosure. Further, it is understood that the method 200 includes steps having features of a typical CMOS technology process flow and those are only described briefly herein.

Figure 3:
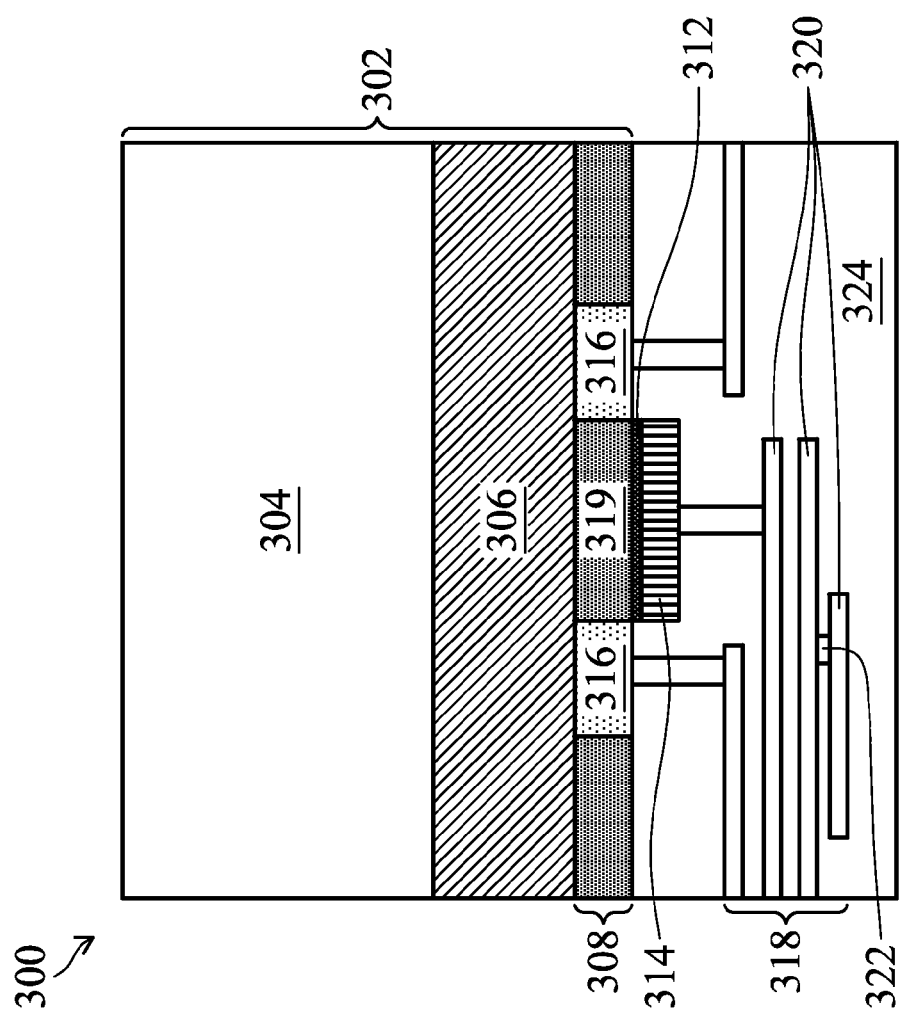
FIGS. 3-14 are cross-sectional views of various embodiments of a BioFET device constructed according to the present disclosure.

The method 200 begins at operation 202 where a substrate is provided. The substrate is a semiconductor substrate. The semiconductor substrate may be a silicon substrate. Alternatively, the substrate may comprise another elementary semiconductor, such as germanium; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP; or combinations thereof. In various embodiments, the substrate is a semiconductor-on-insulator (SOI) substrate. The SOI substrate may include a buried oxide (BOX) layer formed by a process such as separation by implanted oxygen (SIMOX), and/or other suitable processes. The substrate may be doped, such as p-type and n-type. As used herein, workpiece refers to a substrate together with any material bonded or deposited thereon. The semiconductor substrate (or device substrate) refers to the base material on and in which the devices are built and does not include any deposited or bonded material. FIG. 3 is a cross section of a partially fabricated BioFET 300 having a substrate 302. In the example of FIG. 3, the substrate 302 is an SOI substrate including a bulk silicon layer 304, an oxide layer 306, and an active layer 308. The oxide layer 306 may be a buried oxide (BOX) layer. In an embodiment, the BOX layer is silicon dioxide (SiO2). The active layer 308 may include silicon. The active layer 308 may be suitably doped with n-type and/or p-type dopants.

Referring to FIG. 2A, the method 200 then proceeds to operation 204 where a field effect transistor (FET) is formed on the substrate. The FET may be an n-type FET (nFET) or a p-type FET (pFET). The FET includes a gate structure, a source region, a drain region, and a channel region between the source and drain regions. For example, the source/drain regions may comprise n-type dopants or p-type dopants depending on the type of FET. The gate structure includes a gate dielectric layer, a gate electrode layer, and/or other suitable layers. In some embodiments, the gate electrode is polysilicon. Other gate electrodes include metal gate electrodes including material such as, Cu, W, Ti, Ta, Cr, Pt, Ag, Au, suitable metallic compounds like TiN, TaN, NiSi, CoSi, or combinations of these conductive materials. In various embodiments, the gate dielectric is silicon oxide. Other gate dielectrics include silicon nitride, silicon oxynitride, a dielectric with a high dielectric constant (high k), and/or combinations thereof. Examples of high k materials include hafnium silicate, hafnium oxide, zirconium oxide, aluminum oxide, tantalum pentoxide, hafnium dioxide-alumina (HfO2-Al2O3) alloy, or combinations thereof. The FET may be formed using typical CMOS processes such as, photolithography; ion implantation; diffusion; deposition including physical vapor deposition (PVD), metal evaporation or sputtering, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), atomic layer CVD (ALCVD), spin on coating; etching including wet etching, dry etching, and plasma etching; and/or other suitable CMOS processes.

FIG. 3 is a cross section of a partially fabricated BioFET 300 having a substrate 302. The partially fabricated BioFET 300 includes a gate dielectric 312, a gate electrode 314, source/drain regions 316, and active region 319. The source/drain regions 316 and the active region 319 may include opposite-type (e.g., n-type/p-type) dopants. The gate electrode 314 is a polysilicon gate or a metal gate. The gate dielectric 312 is a gate oxide layer (e.g., SiO2, HfO2, or other high k metal oxide).

After forming the FET on the substrate, a multi-layer interconnect (MLI) structure is formed on the substrate. The MLI structure may include conductive lines, conductive vias, and/or interposing dielectric layers (e.g., interlayer dielectric (ILD)). The MLI structure may provide physical and electrical connection to the transistor. The conductive lines may comprise copper, aluminum, tungsten, tantalum, titanium, nickel, cobalt, metal silicide, metal nitride, poly silicon, combinations thereof, and/or other materials possibly including one or more layers or linings. The interposing or inter-layer dielectric layers (e.g., ILD layer(s)) may comprise silicon dioxide, fluorinated silicon glass (FGS), SILK (a product of Dow Chemical of Michigan), BLACK DIAMOND (available from Applied Materials of Santa Clara, Calif.), and/or other insulating materials. The MLI may be formed by suitable processes typical in CMOS fabrication such as CVD, PVD, ALD, plating, spin-on coating, and/or other processes.

Referring to the example of FIG. 3, an MLI structure 318 is disposed on the substrate 302. The MLI structure 318 includes a plurality of conductive lines 320 connected by conductive vias or plugs 322. In an embodiment, the conductive lines 320 include aluminum and/or copper. In an embodiment, the vias 322 include tungsten. In another embodiment, the vias 322 include copper. A dielectric layer 324 is disposed on the substrate 302 including interposing the conductive features of the MLI structure 318. The dielectric layer 324 may be an inter-layer dielectric (ILD layer) or an inter-metal dielectric (IMD) layer and/or composed of multiple ILD or IMD sub-layers. In an embodiment, the dielectric layer 324 includes silicon oxide. The MLI structure 318 provides electrical connection to the gate 314 and/or the source/drain 316.

Referring back to FIG. 2A, in operation 206, an opening is formed at the backside of the substrate. The opening is a trench formed in one or more layers disposed on the backside of the substrate. The opening exposes a region of the substrate underlying the gate and adjacent to the channel region of the FET. The opening may be formed using suitable photolithography processes to provide a pattern on the substrate and etching processes to remove materials form the backside until the body structure of the FET device is exposed. Suitable etching processes include wet etch, dry etch, including plasma etch and/or other suitable processes.

Figure 2B:
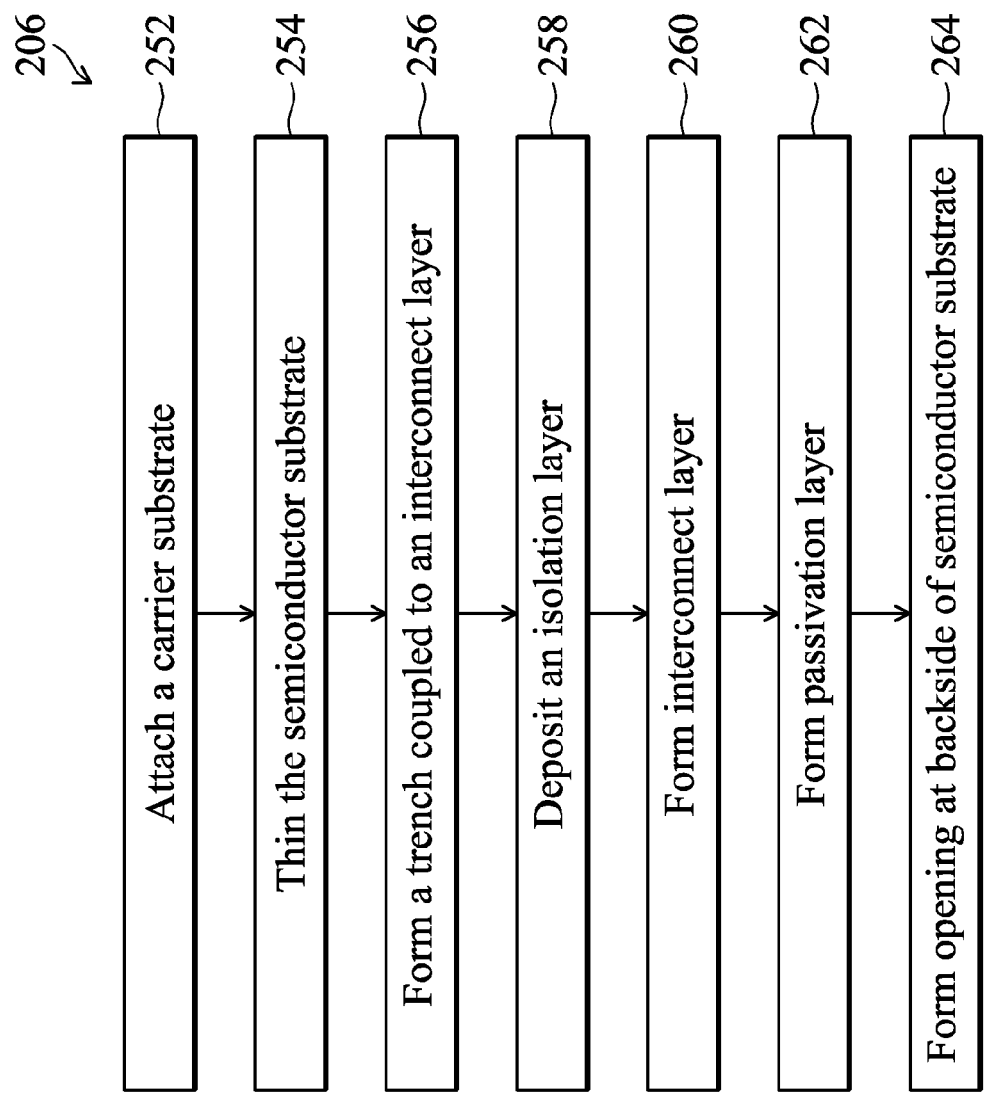
Figure 4:
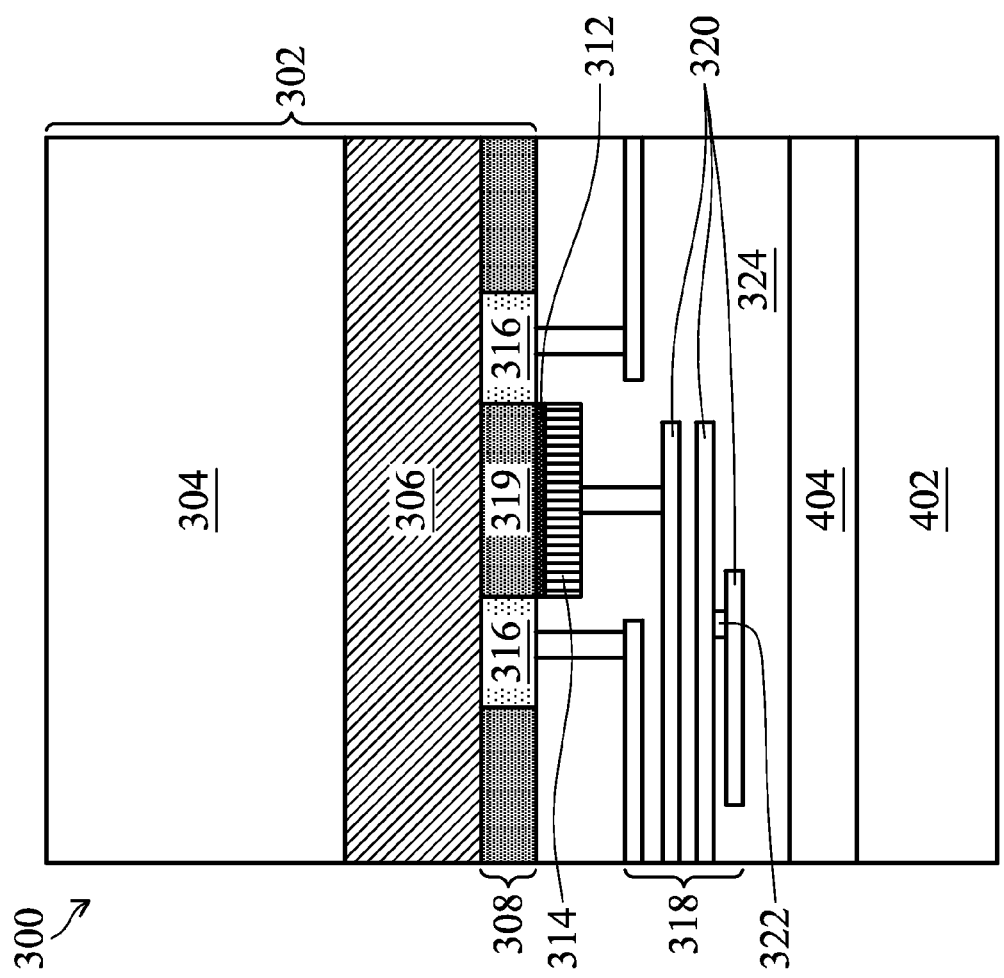

In some embodiments, details of the forming the opening operation includes a number of steps as shown in process diagram of FIG. 2B and cross sections of FIGS. 4 to 10. In operation 252 of FIG. 2B, a carrier substrate is attached. As shown in FIG. 4, a carrier substrate 402 is attached (e.g., bonded) to the device substrate 302. The carrier substrate 402 is attached to the front side of the device substrate 302 over the MLIs. In an embodiment, the carrier substrate is bonded to a passivation layer 404 formed on the MLI and/or ILD layers of the substrate. The carrier substrate may be attached to the device substrate using fusion, diffusion, eutectic, anodic, polymer, and/or other suitable bonding methods. Example carrier substrates include silicon, glass, and quartz. The carrier substrate 402 may include other functionality such as, interconnect features, wafer bonding sites, defined cavities, and/or other suitable features. The carrier substrate may be removed during subsequent processing (e.g., after thinning).

In operation 254 of FIG. 2B, the semiconductor substrate is thinned. The device substrate is flipped and thinned using wet etch processes, dry etch processes, plasma etch processes, chemical mechanical polish (CMP) processes, and/or other suitable processes for removing portions of the semiconductor substrate. Example etchants suitable for thinning the substrate include HNA (hydrofluoric, nitric, and acetic acid), tetramethylammonium hydroxide (TMAH), KOH, buffered oxide etch (BOE), and/or other suitable etchants compatible with CMOS process technology.

Figure 5:
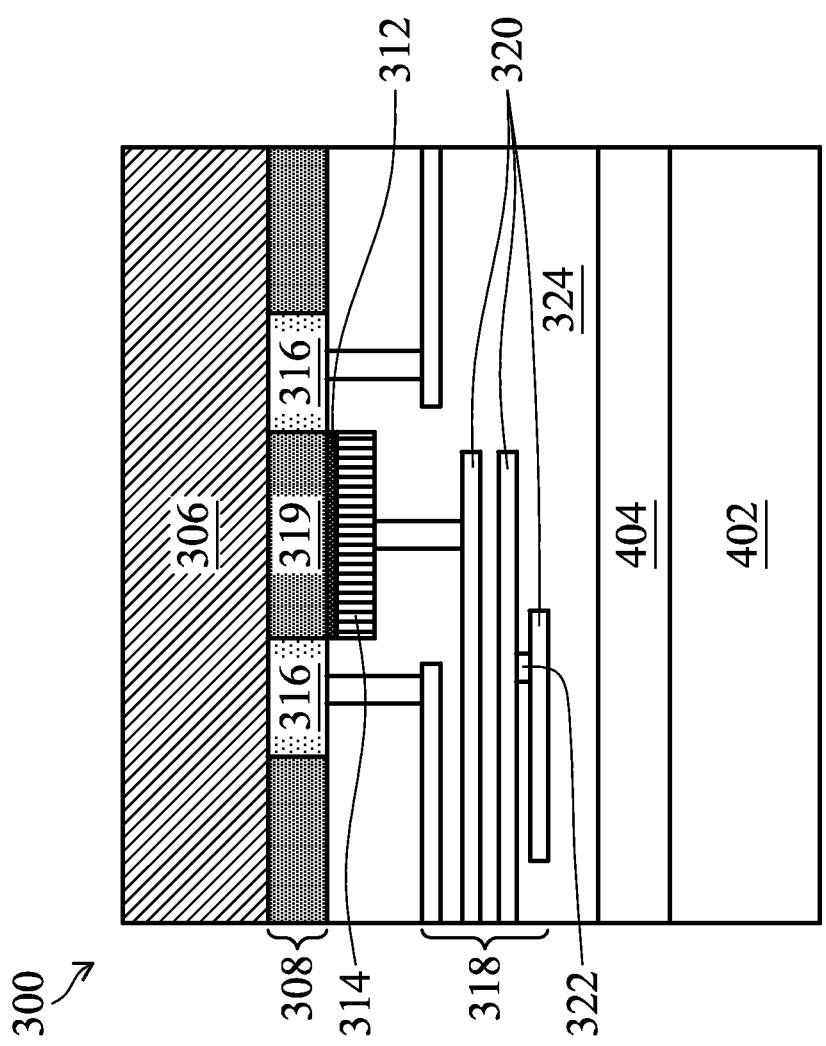
Figure 6:
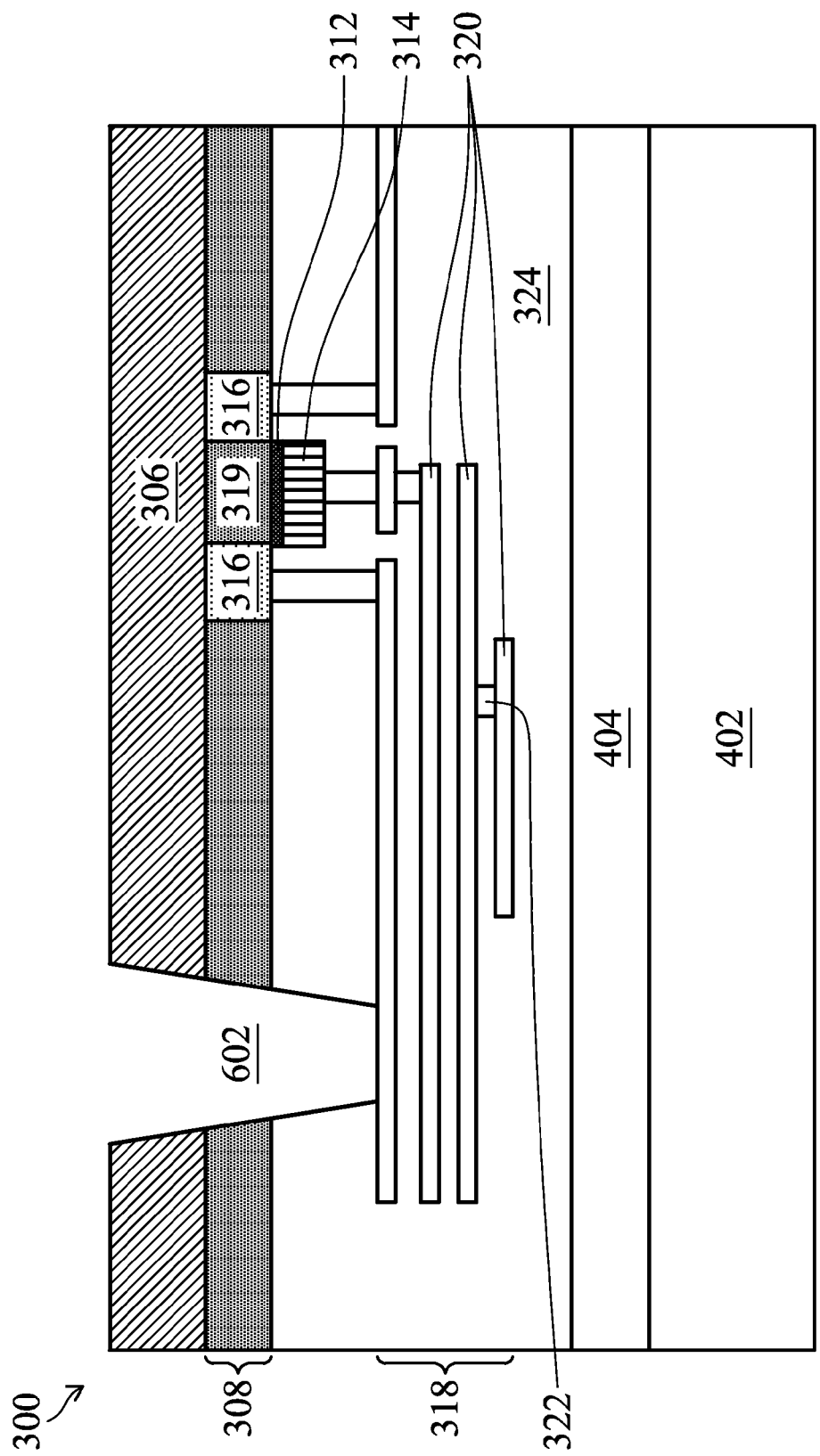

In FIG. 5, the device substrate is thinned such that the bulk silicon layer is removed. In other embodiments both the bulk silicon layer and the buried insulating layer are removed. The device substrate may be thinned in a plurality of process steps, for example, first removing the bulk silicon layer of an SOI wafer followed by removal of a buried insulating layer of the SOI wafer. In an embodiment, a first thinning process includes removal of the bulk silicon using, for example, grinding, CMP, HNA, and/or TMAH etching, which stops at the buried oxide layer. The first thinning process may be followed by a second thinning process, such as BOE wet etch, which removes the buried oxide and stops at the silicon of the active layer. The thinning process may expose an active region of the substrate. In an embodiment, a channel region (e.g., active region interposing the source/drain regions and underlying the gate structure) is exposed. The substrate may have a thickness of approximately 500 Angstroms (A) to 1500 A after the thinning process. For example, in one embodiment the active layer of an SOI substrate has a thickness of between of approximately 500 A and 1500 A.

In other embodiments, the device substrate is thinned such that the bulk silicon layer is removed, and at least a portion of the buried insulating layer remains on the substrate as shown in FIG. 5. The removal of the bulk silicon may be performed using, for example, CMP, HNA, and/or TMAH etching, which stops at the buried insulating layer. The substrate may have a thickness of approximately 500 Angstroms (A) to 15000 A after the thinning process. For example, in one embodiment the active region of an SOI substrate has a thickness of between of approximately 500 A and 1500 A. The buried insulating layer (now providing the surface of the substrate) may be the isolation layer and has a thickness between about 1000 A to a few microns.

In operation 256 of FIG. 2B, a trench is formed on the substrate to expose and provide contact to one or more of the conductive traces of the MLI structure. The trench may be formed by photolithography processes to pattern the trench opening followed by suitable wet, dry or plasma etching processes. In an embodiment, the trench exposes a portion of a metal one (metal 1) layer of the MLI (e.g., the first metal layer formed in the MLI structure after the gate structure is formed). Referring to the example of FIG. 6, a trench 602 is etched, specifically through the active layer 308, to expose a landing region on a conductive line 320 of the MLI structure 318. Alternatively, the trench may be etched through the isolation region 306 (e.g., oxide).

Figure 7A:
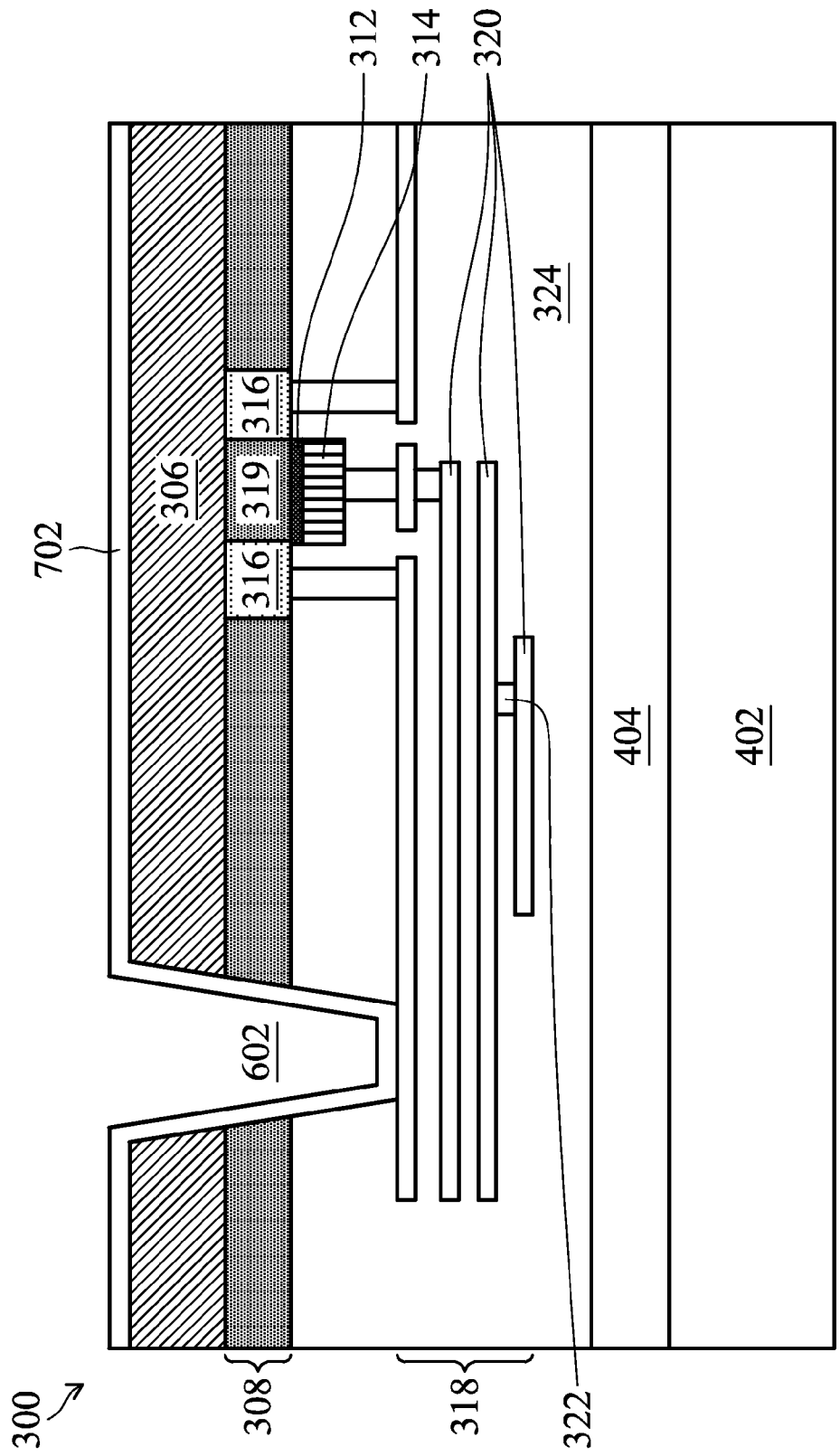
Figure 7B:
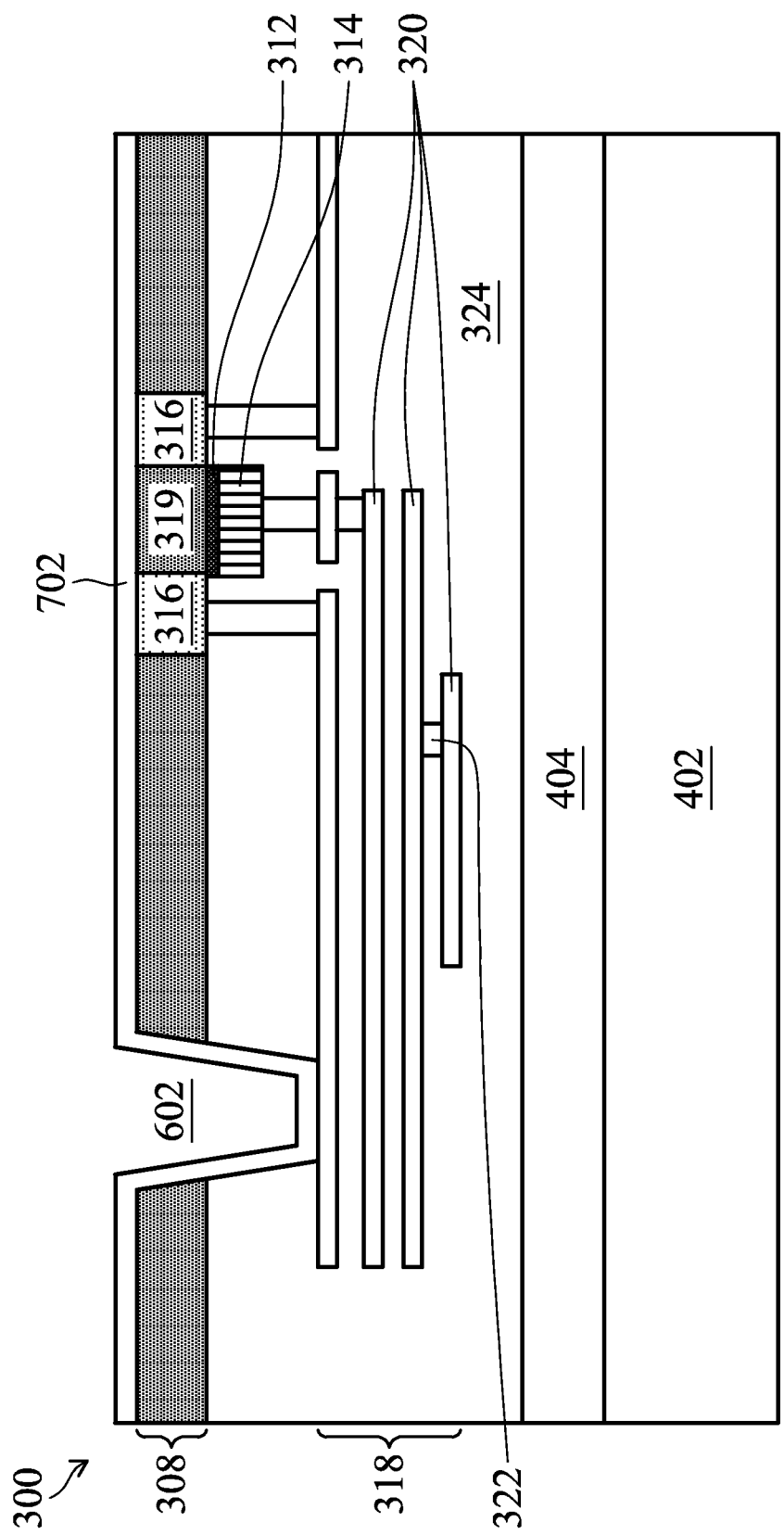
Figure 8:
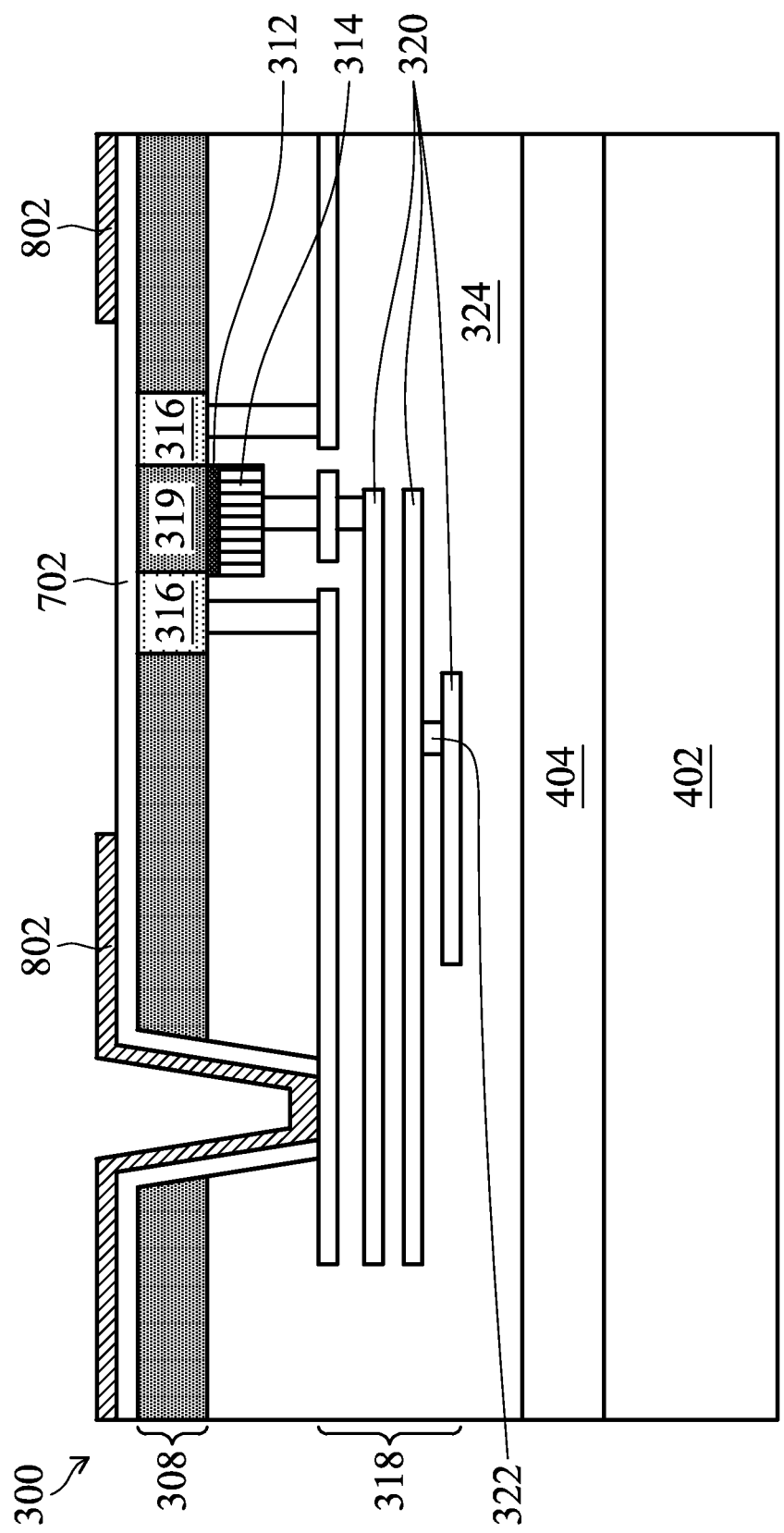

In operation 258 of FIG. 2B, an isolation layer is formed on the substrate. The isolation layer may include a dielectric material such as an oxide or nitride. In an embodiment, the isolation layer is silicon oxide. Referring the example of FIG. 7A, an isolation layer 702 is disposed in the trench 602 and over the insulating layer 306. In an embodiment, the isolation layer 702 is silicon dioxide. As discussed above, in some embodiments, an isolation layer is not formed over the insulating layer if the insulating layer of the SOI substrate was removed during the substrate thinning process. FIG. 7B includes an isolation layer 702 formed in the trench 602 and over the active layer 308 of the of the SOI substrate. The following FIGS. 8-14 illustrate an embodiment wherein BOX layer 306 was removed in the substrate thinning process, such as shown in FIG. 7B. The teaching relating to these figures is equally applicable, however, to embodiments in which all or a portion of BOX 306 (referred to hereafter as insulating layer 306) remains, as shown in FIG. 7A.

In operation 260 of FIG. 2B, an interconnect layer is formed and patterned on the isolation layer 702. One or more openings are patterned and etched in the isolation layer 702 to expose underlying metal or conductive areas. The interconnect layer may provide a connection (e.g., I/O connection) to the MLI structure. The interconnect layer may provide a connection (e.g., I/O connection) to the transistor. The interconnect layer may include a conductive material such as, copper, aluminum, combinations thereof, and/or other suitable conductive material. The interconnect layer may provide functions as a re-distribution layer (RDL). The interconnect layer is formed using metal deposition or plating techniques and then patterned. Referring to the example of FIG. 8, an interconnect layer 802 is disposed on the insulating layer 702. The interconnect layer 802 may provide a signal input/output to the BioFET as well as connecting to the MLI through the trench 602. In an embodiment, the interconnect layer 802 includes an aluminum copper alloy.

In operation 262 of FIG. 2B, a passivation layer is formed on the device substrate. The passivation layer may cover portions of the interconnect layer. The passivation layer may include openings where a bond (e.g., I/O) may be formed. In an embodiment the passivation layer includes silicon dioxide, however, other compositions are possible. The passivation layer may be suitable to provide protection of the device, e.g., the interconnect layer, including from moisture. Referring to the example of FIG. 9, a passivation layer 902 is formed on the substrate including on the interconnect layer 802. The passivation layer 902 includes an opening 904 where a bond (e.g., wire bond, bump) may provide connection (e.g., I/O connection) to the device 300. In other words, the opening 904 may expose a conductive I/O pad.

Figure 9:
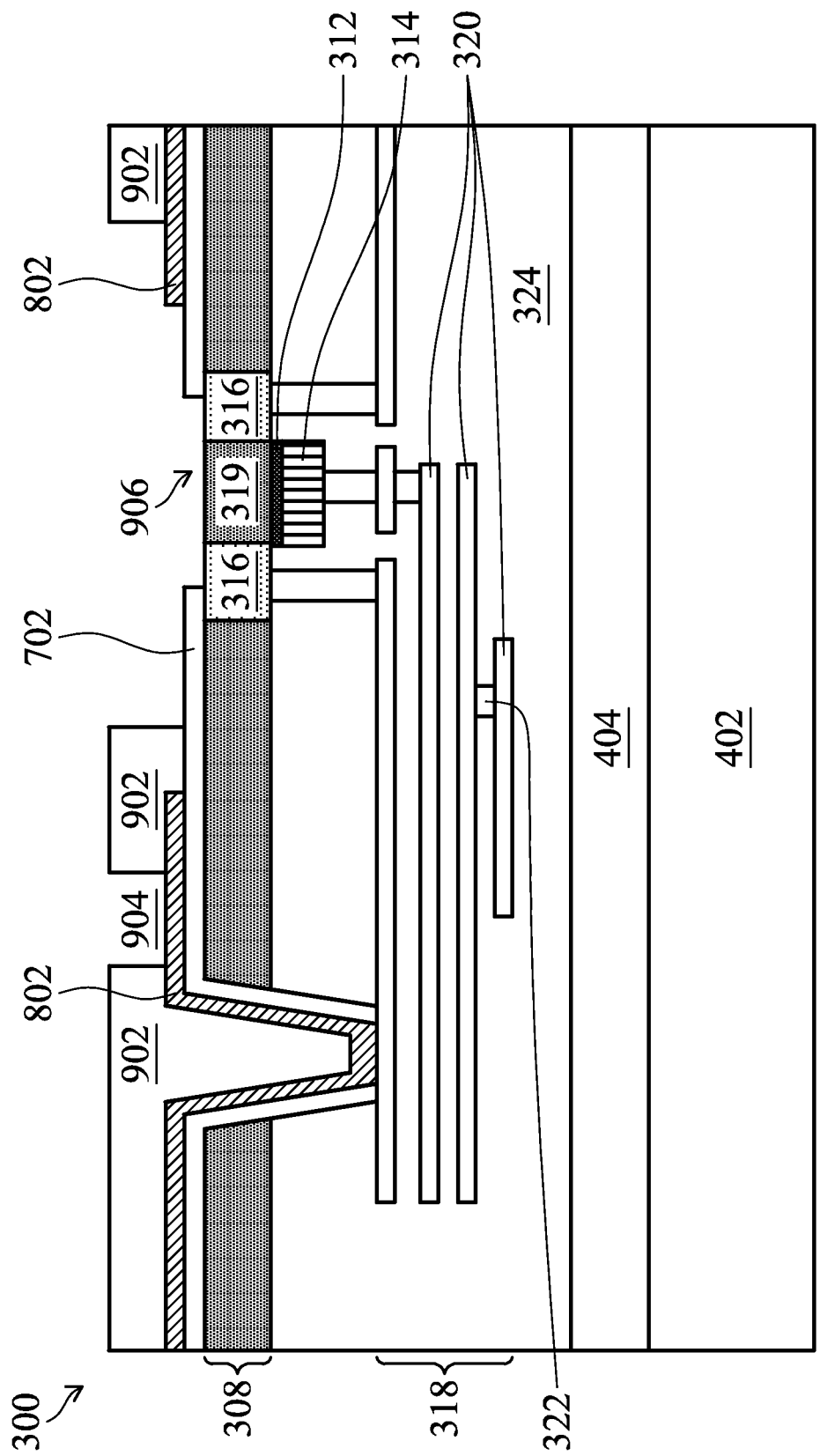

In operation 264 of FIG. 2B, an opening is formed on the backside of the substrate. The opening is formed such that a portion of the active region of the substrate underlying the transistor structure (e.g., channel region) is exposed. The opening is substantially aligned with the active region of the transistor and may be aligned with the back gate structure 312/314. The opening may be formed by suitable photolithography processes followed by an etching process such as a dry etch, wet etch, plasma etch, and/or combinations thereof. In some embodiments, the opening is formed in the isolation layer. In other embodiments, the opening is formed in the buried insulator layer (of the SOI substrate). Referring to FIG. 9, an opening 906 is provided in the isolation layer 702. The opening 906 exposes a portion of the active layer 308. In particular, an active region 319 and portions of source/drain regions 316 may be exposed.

Figure 10:
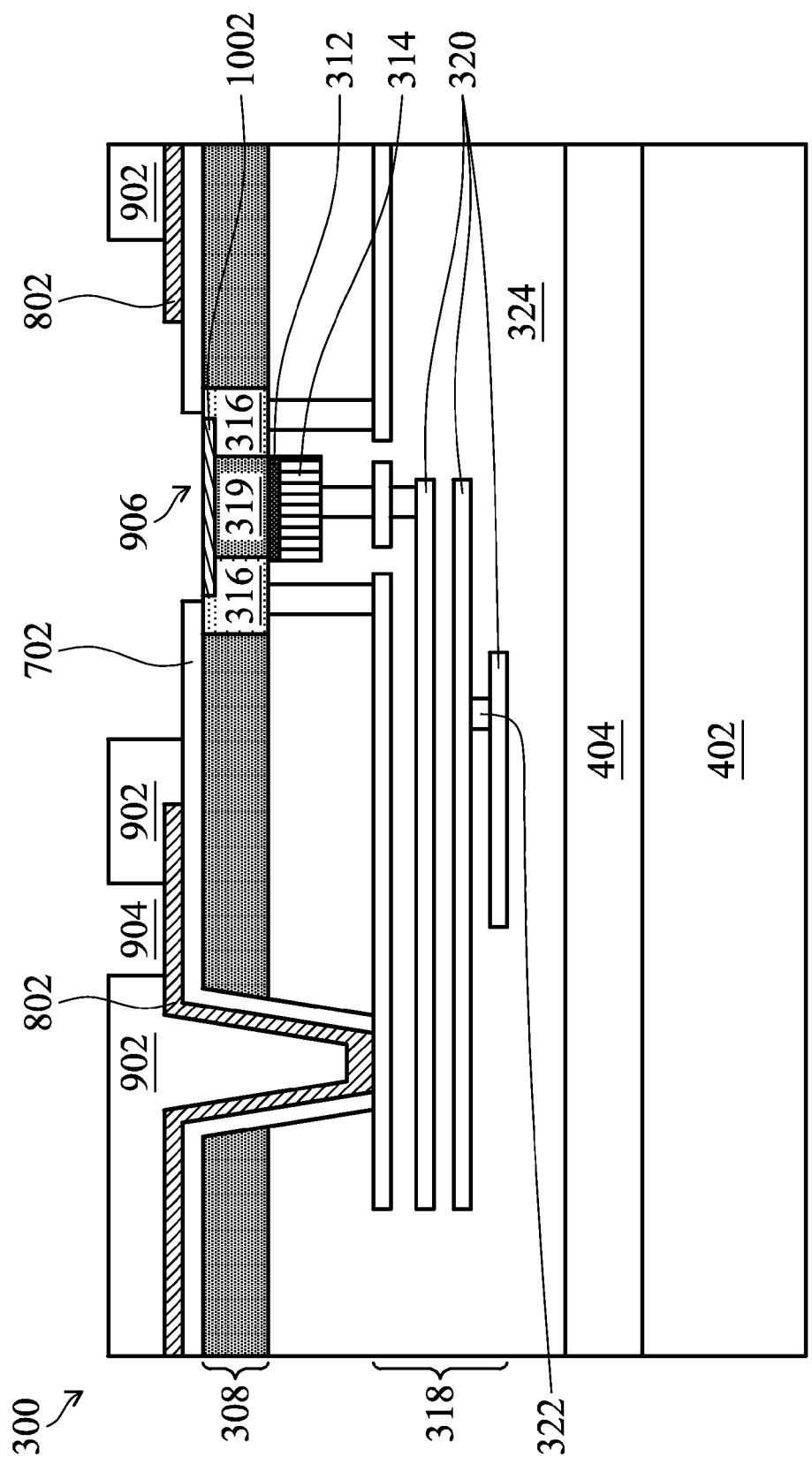

Referring back to FIG. 2A, in operation 207, an exposed substrate area in the opening is treated. The treatment includes at least one of an implant process, a diffusion process, and an anneal process. An implantation process embeds dopants into the surface of the substrate. The depth of the implantation is controlled by an energy of the implantation process. The concentration of dopant in the substrate depends on a dosage of the implantation. Referring to FIG. 10, the implantation process creates a treated layer 1002 at the bottom surface of the opening 906 that has an overall lower net dopant concentration than the rest of the active region 319 below the bottom surface of the opening 906. To achieve an overall lower net dopant, a dopant of an opposite conductivity type from the active region 319 is implanted. For a n-type MOS, arsenic or phosphorous is implanted. For a p-type MOS, boron is implanted. Because these dopants have an opposite conductivity type from the active region 319, the overall net dopant concentration is reduced at the surface of the active region 319. The treated layer is then a lightly doped channel layer as compared to the rest of the active region. If sufficient dopants are implanted, the treated layer is then a depleted layer. A relatively low energy implantation process may be used to confine the dopants to a surface layer. For example, the implantation energy may be less than about 10 keV or less than about 15 keV. If the active region 319 is sufficiently thick and a larger treated layer is to be created, a higher energy may be used. According to various embodiments, the treated layer has a peak concentration at about 5 angstroms or a few hundred angstroms from the surface. A thickness of the treated layer may be between about 10 nanometers to a few hundred nanometers.

The implantation process may be performed directly on the substrate or through a mask. An implantation mask may be formed first by depositing a sacrificial oxide layer, which is then patterned to form an opening for the implantation. The mask creation may be performed with operation 206 where opening 906 is formed. In some embodiments, the opening 906 is larger than the implantation opening. For example, the treated layer 1002 may extend to a portion of the source drain 316 or be confined to a surface of the active region 319.

In some embodiments, the insulation layers 306 and passivation layers 902 are sufficient to block the dopants from embedding in other portions of the BioFET. In one embodiment, the operation 262 of FIG. 2B is performed without forming the opening 904 to protect the interconnect layer 802 from the implantation. In these embodiments, openings 904, 906 in the passivation layer 902 are formed after the implantation.

After the implantation, the substrate is annealed to activate the dopant. Different dopants require different amounts of annealing to activate. Lower temperature anneals activate at a reduced rate. Because the activation anneal occurs after the MLI 318 and interconnect layer 802 are formed, the stability and contamination of the metal material in the device are balanced against the activation rate. In some embodiments, the implantation and activation anneal are performed before the interconnect layer 802 is formed. The activation anneal may be performed at about 400 degrees Celsius, about 450 degrees Celsius, and may be less than about 500 degrees Celsius. In some embodiments, a laser is used to activating the dopants. Because the laser energy may be focused at the surface of the substrate and the laser exposure is very short in duration, often less than one microsecond, the laser activation may be performed without significant adverse effects to the much deeper MLI 318. In one embodiment, a laser beam scans the die. In another embodiment, a laser beam is adjusted to have a size that is sufficient to activate the dopants one die at a time.

Alternatively, the treated layer 1002 may be formed by adding a dopant that tends to deactivate the primary dopant of the active region 319. In a nMOS example, hydrogen may be added to create a treated layer 1002 because hydrogen can deactivate boron. The hydrogen may be implanted just as arsenic, phosphorous, and boron. Hydrogen may also be added by a diffusion process. One diffusion process involves annealing in a hydrogen environment (hydrogen/deuterium gas or forming gas) or applying hydrogen plasma to the surface. Another diffusion process involves depositing a highly-doped dielectric layer in the opening 906 over the active region 319 and then annealing for the doped hydrogen to diffuse into silicon. The highly-doped dielectric layer may be a silicon oxide or a silicon nitride film. After the diffusion anneal, the dielectric layer is removed.

In addition to the implantation and diffusion methods to form the treated layer 1002, a treated layer 1002 may be formed by annealing in an oxygen or ozone environment. The anneal repairs dangling bonds caused by plasma processes. Anneals in an oxygen atmosphere of oxygen or ozone repairs dangling bonds. A treated layer 1002 may also be formed by annealing in a hydrogen environment. Anneals in a hydrogen atmosphere of hydrogen or deuterium mitigates mobile ions from plasma-induced damage. Anneals for mitigation of mobile ions are at a lower temperature than the diffusion anneal described above and may be combined into one step.

The treated layer 1002 allows electrical property tuning of the BSS BioFET. When the treated layer 1002 is a lightly doped layer or a depleted layer, the BSS BioFET can be made more sensitive to molecules bound to receptors, improving the transconductance of the BSS BioFET. In other words, the drain current for a gate voltage may be increased relative to a BioFET without treated layer 1002. In some embodiments, the treated layer 1002 provides a larger bandgap which can avoid or reduce current leakage. In some embodiments, the treated layer 1002 includes fewer defects than untreated layers and can reduce device noise from mobile ions and interfacial charges. A number of BioFETs on a same device may be tuned to different sensitivities with for the same or different bio-entities by changing the process of forming the treated layer. For example some of the BioFETs may have a treated layer having a first dopant at a first concentration and other BioFETs may have a treated layer having a second dopant at a second concentration. The different treated layer allows the BioFETs to detect targets differently. By using different masks and separate lithography steps, more than one type of treated layers can be formed on one device.

Figure 11:
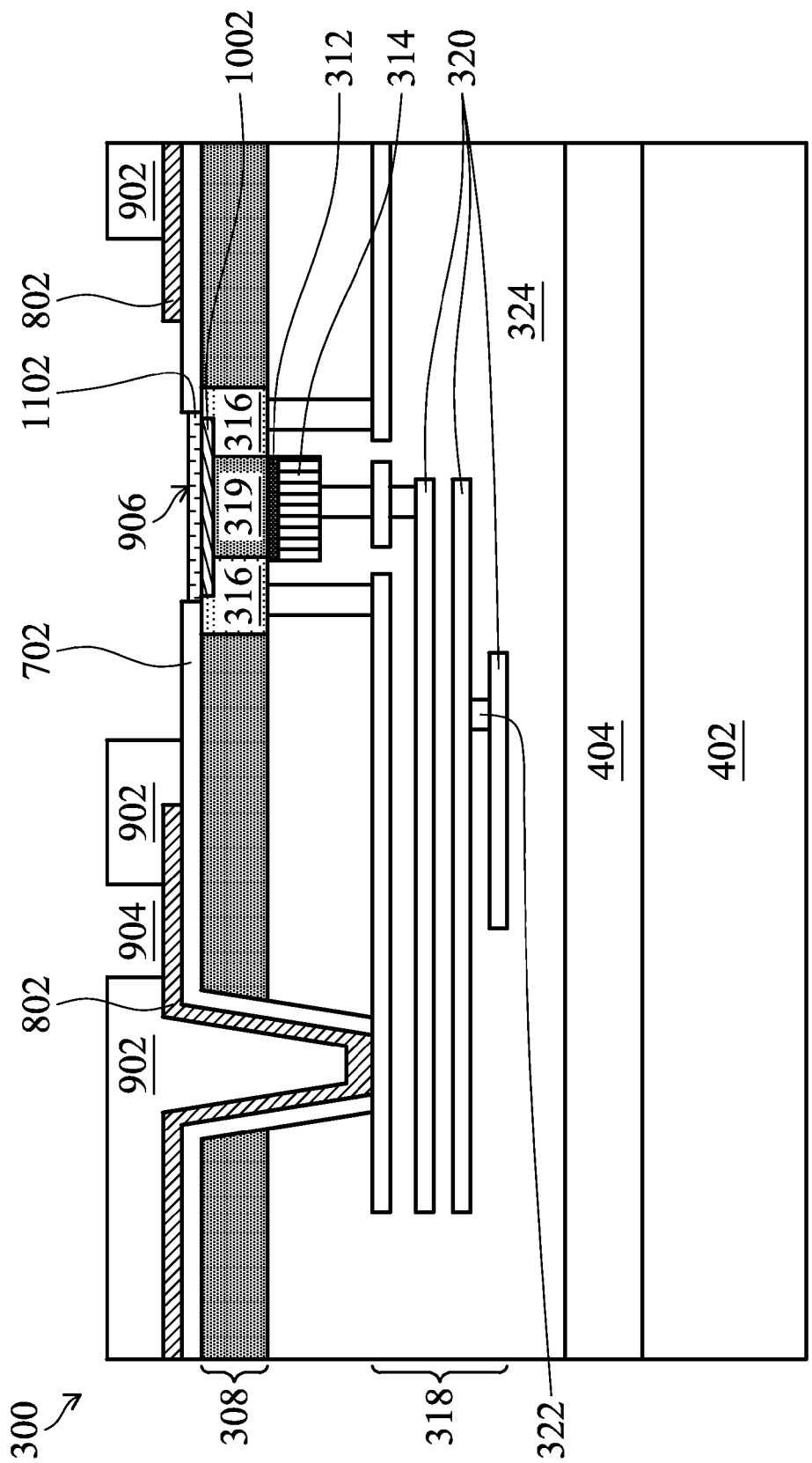

Referring back to FIG. 2A, in operation 208 a dielectric layer is formed in the opening. The dielectric layer is formed on the exposed substrate underlying the gate structure of the FET and covers the entire bottom of the opening 906 over the treated layer 1002. Exemplary dielectric materials include high-k dielectric films, metal oxides, and/or other suitable materials. Specific example of dielectric materials include $HfO_2$, $Ta_2O_5$, $Au_2O_3$, $WO_3$, oxides of Pt, Ti, Al, and Cu, and other dielectrics such as $SiO_2$, $Si_3N_4$, $Al_2O_3$, $TiO_2$, TiN, SnO, SnO2, among others. The dielectric layer may be formed using CMOS processes such as, for example, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), or atomic layer CVD (ALCVD). In some embodiments, the dielectric layer includes a plurality of layers. For example, a dielectric layer may include a hafnium oxide layer over an aluminum oxide or titanium oxide layer. In the example of FIG. 11, a dielectric layer 1102 is disposed over the active layer 319 and a portion of the source and drain 316. The dielectric layer 1102 can be patterned to be aligned with the gate structure (e.g., is disposed and patterned to remain only in the opening 906.)

Referring back to FIG. 2A, in optional operation 210 a metal layer is deposited. The metal layer may be an elemental metal, metal alloy, or a conductive metallic compound. Suitable elemental metals include tantalum, niobium, tungsten, ruthenium, aluminum, zirconium, vanadium, titanium, cobalt, molybdenum, osmium, chromium, rhodium, gold, palladium, rhenium, nickel, or other transition metal commonly used in semiconductor process. The metallic compound includes conductive nitride, silicide, and oxides of these transition metals. For example, tungsten nitride, tantalum nitride, and ruthenium oxide. The metal layer may be a composite layer of two or more layers. For example, the metal layer may include both tungsten nitride and ruthenium oxide.

The metal layer is deposited conformally over the substrate and in the opening covering the interface layer. The metal layer may be deposited using a PVD (sputtering), metal chemical vapor deposition (MCVD), atomic layer CVD (ALCVD), electrochemical deposition with a seed layer, or electroless deposition. In some embodiments, an ion beam deposition may be used to selectively deposit the metal layer in and around the opening.

In optional operation 212, the metal layer is patterned to form a metal crown structure. In some embodiments, the patterning involves removing, by etching, unwanted portions of the metal layer deposited in operation 210. An etch mask is first deposited and patterned. The etch mask may be a photoresist or a hardmask patterned by a photolithography process. In other embodiments, a photoresist material is first deposited and patterned on the substrate and removed after the metal layer is deposited. Lifting off the photoresist material also removes any overlying metal layers. The lift-off technique may be useful when the dry etch involving plasma to remove the metal pattern would cause undesirable amounts of plasma-induced damage to other exposed metal surfaces. Because the photoresist in the lift-off process may be removed with just wet etching or including low-power plasma etching, it is sometimes preferred over the metal patterning technique. However, the lift-off process has the potential to produce more contaminants and a shape of the resulting metal crown structure may include jagged edges.

Figure 12:
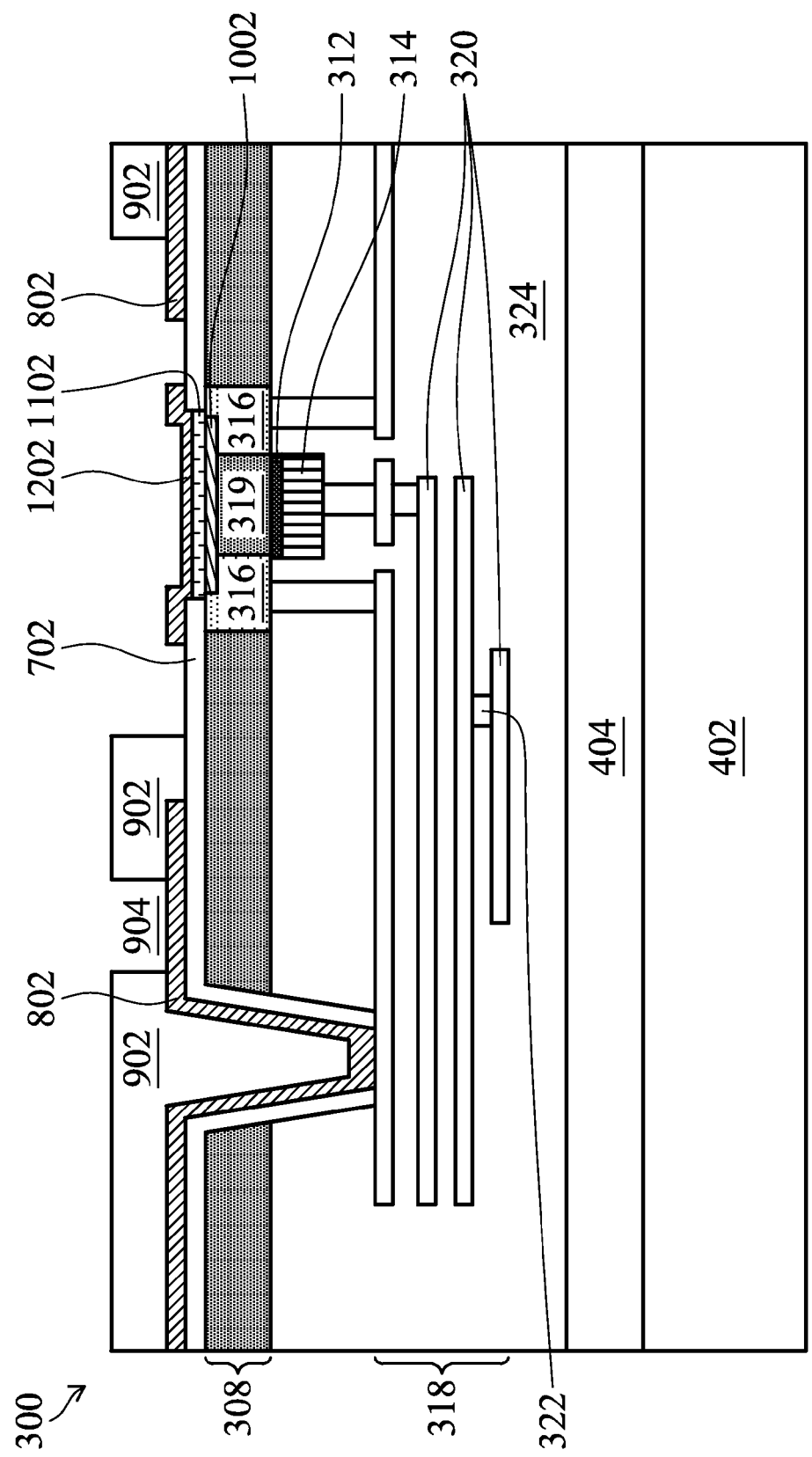
Figure 13:
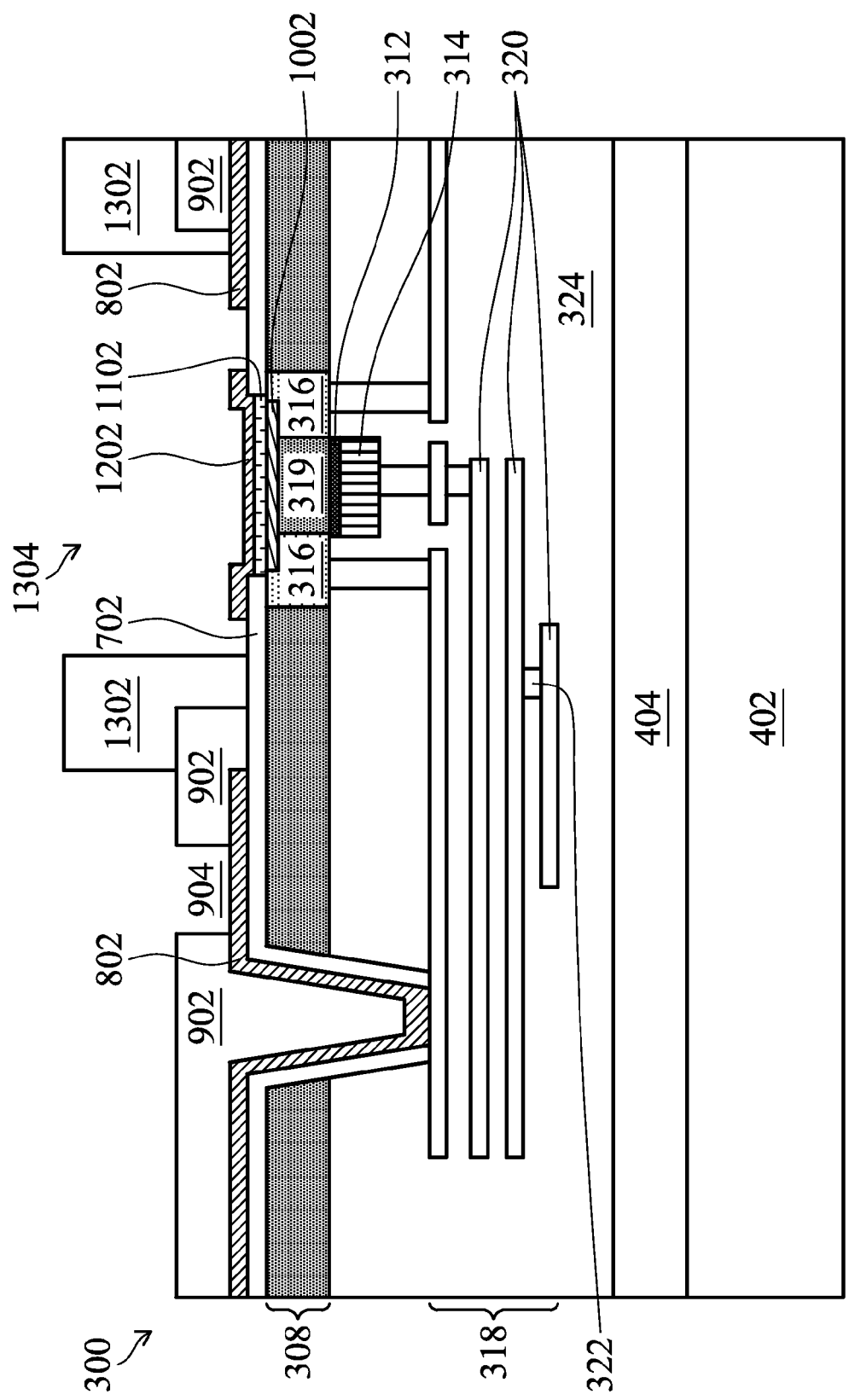

In the example of FIG. 12, a metal crown structure 1202 is disposed over a dielectric layer 1102 in and around the opening. As shown, the metal crown structure 1202 includes a lip that overlaps a portion of the isolation layer 702. In some embodiments all of the metal crown structure 1202 is within the opening 906 of FIG. 11. In other embodiments, the dielectric layer 1102 and metal crown structure 1202 consumes the volume of the opening as shown in FIG. 12.

Referring back to FIG. 2A, in operation 214 a microfluidic channel or well is disposed on the device substrate. The fluidic channel defines a region overlying the metal crown structure through which the analyte flows. The fluidic channel may be formed by lithography utilizing SU-8 (an epoxy negative photoresist), wafer bonding methods, and/or other suitable methods. Referring to the example of FIG. 13, a fluidic channel 1302 is disposed on the substrate. The fluidic channel 1302 provides a well 1304 overlying the metal crown structure 1202.

Figure 14:
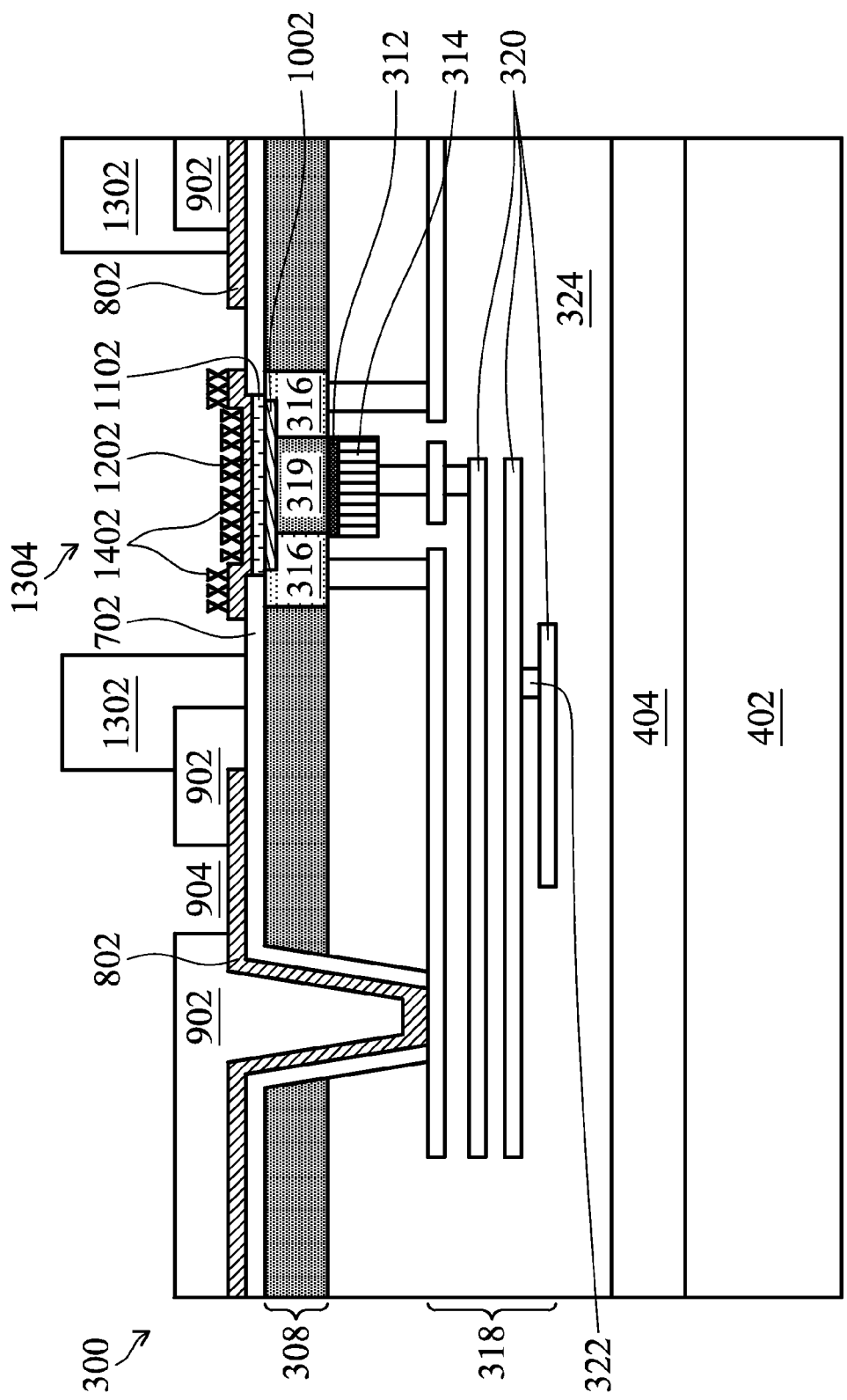

Referring back to FIG. 2A, in operation 216, a receptor or film treatment is disposed on the metal crown structure. The receptor may include enzymes, antibodies, ligands, protein, peptides, nucleotides, and portions of these. The receptor may be a modified form of a native protein or enzyme configured on one end to detect a specific analyte. The other end of the receptor is configured to bond to the metal crown structure or another molecule/film treatment that is bonded to the metal crown structure. As shown in FIG. 14, a plurality of receptors 1402 is disposed on metal crown structure 1202. By using a metal crown structure, a larger surface area is available to receptors for bonding and hence more sites are available for biomolecule or bio-entity detection. If the metal crown structure is not used, then the receptors are disposed on the dielectric layer 1102 directly or through another molecule/film treatment. Operation 216 may be performed before operation 214 in certain embodiments.

The embodiments of FIG. 2B pertain to aspects of the present disclosure where the electrical connections for the BioFET device are made on the same side of the substrate as the fluidic connections. The present disclosure also pertains to embodiments where the electrical connections for the BioFET device are made to the opposite side of the substrate as the fluidic connections. In those embodiments, electrodes and pads are formed connecting to the MLI on the front side of the substrate before the carrier substrate is bonded and device substrate thinned. From the backside, trench 602 is not formed.

During operation of the BioFET device, a solution that contains target molecules is provided in the fluidic channel. The BioFET device may contain different areas for processing the target molecule. Some bio-material may be lysed, separated, dyed, and otherwise tested or analyzed using chemical, electrical, or optical means. For example, a drop of blood may be inserted in an inlet and initially separated by plasma and cell type. Certain cells in the blood drop may be lysed. Some macromolecules in the lysate may be further broken down for analysis downstream in the flow path. Deoxyribonucleic acid (DNA) molecules may be fragmented by enzyme reaction, restriction or shearing into target strands.

After processing the bio-material into targets, the targets are detected by flowing through microfluidic channels and wells containing the BioFETs. Either the dielectric layer 1102 or the metal crown structure 1202, if used, is the sensing surface of the BioFET. The flow may be controlled such that the targets have a long residence time in the presence of the sensing surfaces as compared to the reaction time. In some embodiments, one or more gate bias is varied while the current flown through the BioFET is collected. The electrical information from the BioFET are collected and analyzed.

In various embodiments, a CMOS fabrication facility (e.g., foundry) may process the methods in accordance with various embodiments for the associated device up to the fluidic channel formation. In an embodiment, a subsequent user may provide the surface treatment technologies, ionic solutions, receptors, and the like.

In summary, the methods and devices disclosed herein provide a BioFET that is fabricated using CMOS and/or CMOS compatible processes. Some embodiments of the disclosed BioFET may be used in biological and/or medical applications, including those involving liquids, biological entities, and/or reagents. One detection mechanism of some embodiments described herein includes a conductance modulation of the FET of the BioFET due to the binding of the target bio-molecule or bio-entity to the fluidic gate structure, or a receptor molecule disposed (e.g., immobilized) on the fluidic gate structure of a device.

Some embodiments of the BioFETs are arranged in an array form. The gate structures may be built on silicon-on-insulator (SOI) substrates. This may provide advantages in some embodiments of operation at a higher speed and/or consumption of less power. The inverted transistor provided on an SOI substrate may achieve improved fabrication uniformity, have improved process control, and increase the BioFET density. Some embodiments may provide for an improved short-channel effect, for example, due to the formation on a SOI substrate. Other features include lower current leakage, lower power consumption, and lower device noise from irradiation processes.

Thus, it will be appreciated that in one embodiment a BioFET device is described that includes a substrate, a transistor structure in the substrate including a treated layer next to a channel region in the active region, an isolation layer with an opening on a side of the substrate opposite from a gate structure of the transistor, and an dielectric layer in the opening. The transistor structure has a gate structure over a source region, a drain region, and an active region including a channel region and a treated layer.

One aspect of the present disclosure pertains to a semiconductor device is provided that includes an array of BioFET devices. A first and second plurality of BioFET devices in the array include an active region between a source and a drain region and underlying a gate structure. The active region including a channel region that adjoins the gate structure and a treated layer. The treated layer in the first plurality of BioFET devices has a first dopant at a first concentration. The treated layer in the second plurality of BioFET devices has a second dopant at a second concentration. The first and second plurality of BioFET devices also include a dielectric layer disposed on a side of the treated layer opposite from the channel region.

Another aspect of the present disclosure pertains to a method of fabricating a BioFET device includes forming a transistor on a semiconductor substrate, etching an opening in an isolation layer disposed on a second side of the semiconductor substrate that exposes the active region of the transistor, embedding a dopant into the active region of the transistor through the bottom of the opening to form a treated layer, and depositing an dielectric layer on the treated layer. The embedding may be accomplished by implant a dopant having an opposite conductivity from a dopant in the channel region, implanting hydrogen, and diffusing one or more dopants through annealing a highly doped sacrificial layer. The method may also include annealing the semiconductor substrate in an oxygen or hydrogen environment.

In describing one or more of these embodiments, the present disclosure may offer several advantages over prior art devices. In the discussion of the advantages or benefits that follows it should be noted that these benefits and/or results may be present is some embodiments, but are not required. Advantages of some embodiments of the present disclosure include the ability to offer a customer-customizable product. For example, fluidic channel formation, receptor introduction and the like may be performed by a customer. As a further example of advantages of one or more embodiments described herein, in conventional devices it is typical to require high aspect ratio processing to form a bio-compatible interface (e.g., requiring etching from a front surface of the substrate to a gate structure). Because the present methods provide for processing on a backside of a thinned wafer, the aspect ratio is reduced.

What is claimed is:

1. A biological field-effect transistors (BioFET) device, comprising:
   a substrate;
   a transistor structure in the substrate having a gate structure over a source region, a drain region, and an active region, the active region including a channel region and a treated layer;
   an isolation layer on a side of the substrate opposite from the gate structure, said isolation layer having an opening at the active region of the transistor structure; and
   a dielectric layer in the opening.

2. The BioFET device of claim 1, wherein the treated layer is a lightly doped layer.

3. The BioFET device of claim 1, wherein the treated layer comprises a dopant having a conductivity type opposite from a dopant in the channel region.

4. The BioFET device of claim 1, wherein the treated layer comprises hydrogen.

5. The BioFET device of claim 1, further comprising a metal crown structure over the dielectric layer and at least partially covering sidewalls of the opening.

6. The BioFET device of claim 1, wherein the dielectric layer comprises aluminum oxide, titanium oxide, hafnium oxide, tantalum oxide, tin oxide, or a combination of these.

7. The BioFET device of claim 1, further comprising:
   a fluidic channel disposed on the isolation layer.

8. The BioFET device of claim 1, further comprising:
   a multi-layer interconnect (MLI) disposed in the substrate on a side of the substrate that is same as the gate structure.

9. The BioFET device of claim 8, wherein a carrier substrate is bonded to the substrate via a passivation layer over the MLI.

10. A biological field-effect transistors (BioFET) device, comprising:
    a substrate comprising an active region between a source and a drain region, the active region including a channel region and a treated layer;
    a gate structure overlying the active region, wherein the channel region adjoins the gate structure; and
    a dielectric layer disposed on a side of the treated layer opposite from the channel region and further comprising an isolation layer on a side of the substrate opposite from the gate structure, said isolation layer having an opening at the treated layer and the dielectric layer being disposed in the opening.

11. The BioFET device of claim 10, further comprising a metal crown structure disposed over the dielectric layer.

12. The BioFET device of claim 11, further comprising a receptor bonded to the metal crown structure.

13. The BioFET device of claim 10, further comprising a multi-layer interconnect (MLI) disposed in the substrate on a side of the substrate that is same as the gate structure.

14. The BioFET device of claim 13, further comprising a trench in the substrate to provide an external electrical connection the MLI.

15. The BioFET device of claim 10, further comprising a microfluidic channel disposed on the substrate.

16. The BioFET device of claim 10, wherein the treated layer is a lightly doped layer.

17. The BioFET device of claim 10, wherein the dielectric layer comprises aluminum oxide, titanium oxide, hafnium oxide, tantalum oxide, tin oxide, or a combination of these.

* * * * *